United States Patent [19]

Puhler et al.

[11] Patent Number: 4,626,504
[45] Date of Patent: Dec. 2, 1986

[54] DNA TRANSFER VECTOR FOR GRAM-NEGATIVE BACTERIA

[75] Inventors: Alfred Puhler; Reinhard Simon, both of Bielefeld, Fed. Rep. of Germany

[73] Assignee: Lubrizol Genetics, Inc., Boulder, Colo.

[21] Appl. No.: 510,370

[22] Filed: Jul. 1, 1983

[51] Int. Cl.[4] ................. C12N 15/00; C12N 1/20; C12N 1/00

[52] U.S. Cl. ...................... 435/172.3; 435/253; 435/317; 935/29; 935/30; 935/55; 935/67; 935/72

[58] Field of Search ............ 435/172.3, 253, 317, 435/878; 935/22, 23, 26, 27, 29, 30, 66, 72

[56] References Cited

PUBLICATIONS

Simon, R. et al., Bio/Technology, Nov., 1983, "A Broad Host Range Mobilization System for in vivo Genetic Engineering: Transposon Mutagenesis in Gram Negative Bacteria".
Simon, R. et al in Molecular Genetics of the Bacteria—Plant Interaction, (A. Puhler, ed.), pp. 98–106, 1983, Springer-Verlag, publisher.
Simon et al, "Analysis of Plasmid Borne Genes in Rhizobium meliloti by Tn5 Mutagenesis", Winnipeg Symposium-Proc. 8th N. Amer. Rhizobium Conf. (meeting held in 1981).
Bagdassarian et al, Gene, vol. 16, pp. 237–242 (1981).
Bagdassarian et al., Microbial Drug Resistance, Proc. 3rd Int'l Simp., Tokyo, S. Mitshuhashi (ed) pp. 183–197 (1982).
Chang, et al, J. Bact., vol. 134, pp. 1141–1156 (1978).
8th North American Rhizobium Conference Abstract Book, pp. 1–3, 7–15, 20, 22, 25, 28–29, 42–43, 100–103, 105, 128, 130, 132 and 136 (Aug. 3–7, 1981).
Proceedings, 8th North American Rhizobium Conference, pp. 90–114 (K. W. Clark & J. H. G. Stephens, eds., 1983).
Datta, N., et al. (1971) J. Bact., 108:1244–1249.
Datta, N. and R. W. Hedges (1972) J. Gen. Microbiol., 70:453–460.
Olsen, R. H. and P. Shipley (1973) J. Bact., 113:772–780.
Beringer, J. G. (1974) J. Gen. Microbiol., 84:188–198.
Beringer, J. E., et al. (1978) Nature, 276:633–634.
Priefer, U. B., et al. (1980) In Antibiotic Resistance, Transposition and Other Mechanisms (S. Mitshuhashi, L. Rosival and V. Krcmery, eds.) Springer-Verlag, Berlin, pp. 91–96.
Simon, R. (1980) In Antibiotic Resistance, Transposition and Other Mechanisms (S. Mitshuhashi, L. Rosival and V. Krcmery, eds.) Springer-Verlag, Berlin, 35–42.

Primary Examiner—Thomas G. Wiseman
Assistant Examiner—Jayme A. Huleatt
Attorney, Agent, or Firm—Lorance L. Greenlee

[57] ABSTRACT

Modified E. coli vectors are disclosed that are mobilizable to a wide range of gram-negative bacteria, but are not self-transmissible. The modified E. coli plasmids replicate only in bacterial strains of the E. coli group. Mobilizer strains of E. coli are also provided, as well as methods for employing the modified E. coli vectors for transposon mutagenesis, site-specific gene transfer, and the construction of DNA libraries.

22 Claims, 4 Drawing Figures

FIG. 1  Construction of an RP4-Mobilisator-strain
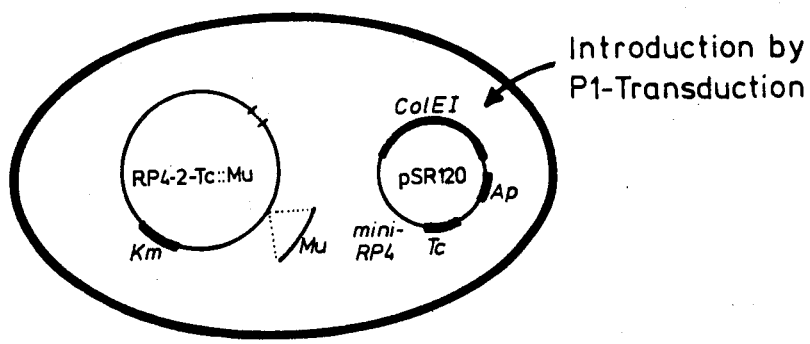
Coselection on KmTc in recA⁻ backround
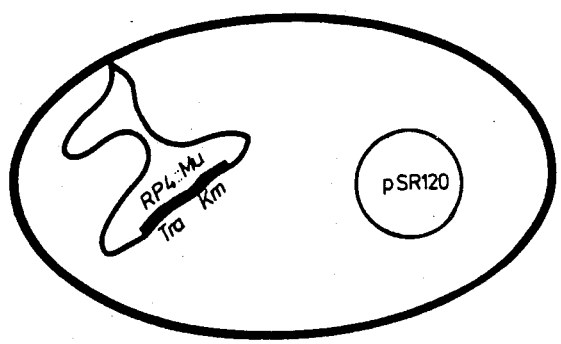
Spontaneous integration of RP4 into the chromosome
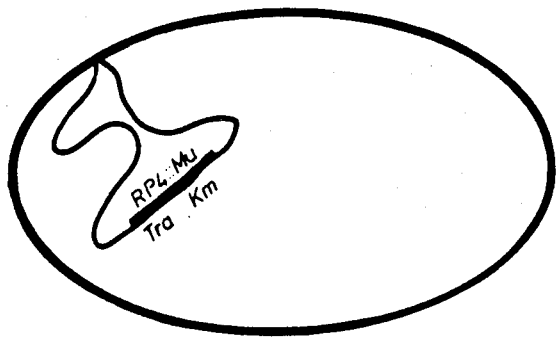
Curing of pSR120

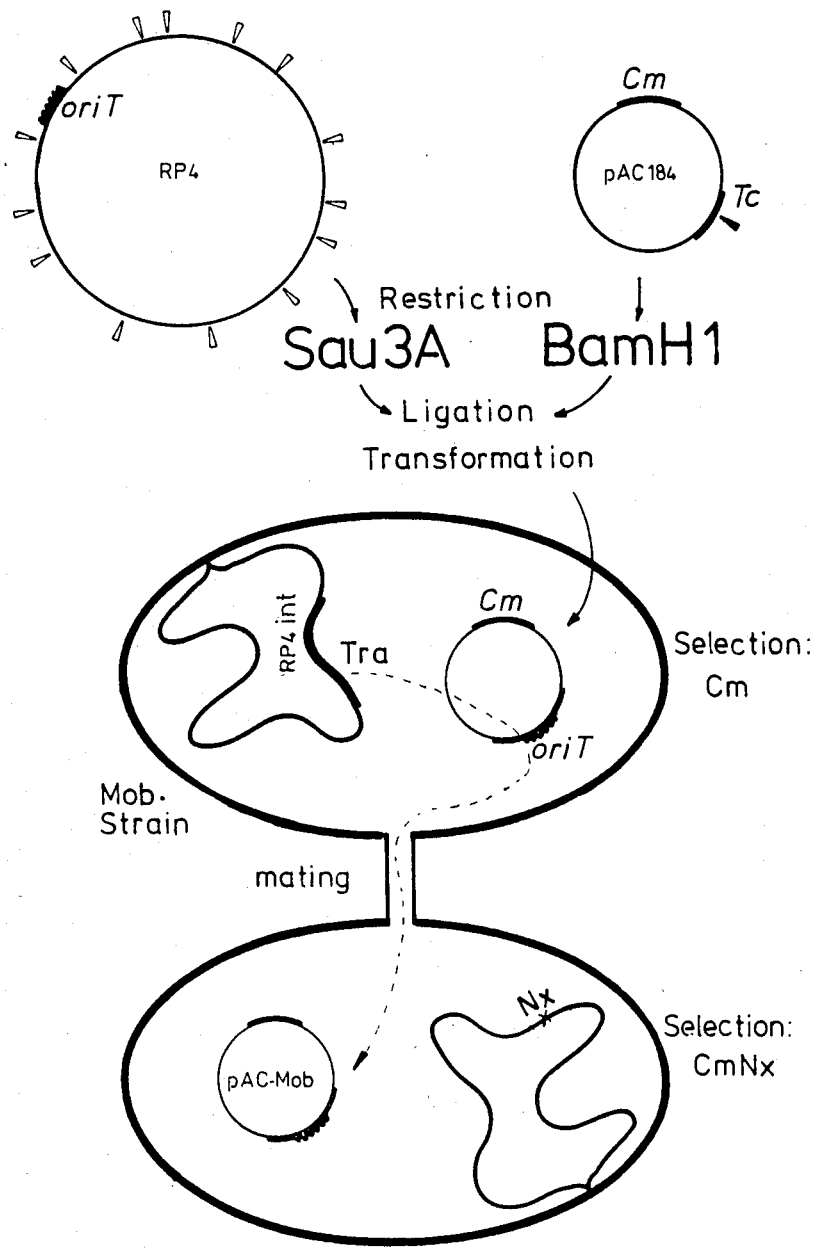
FIG. 2 Cloning of the RP4-Mob-site ($ori_T$) into pACYC184

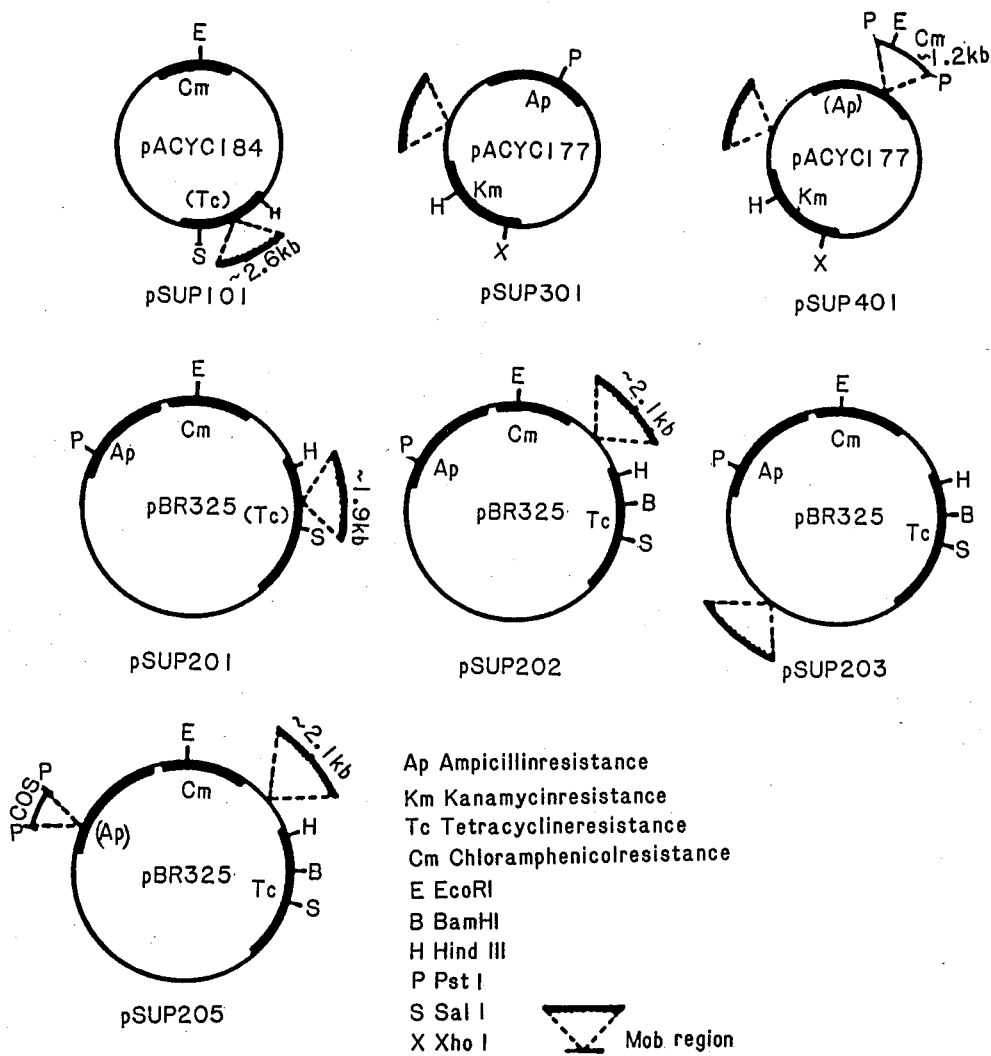

DNA TRANSFER VECTOR FOR GRAM-NEGATIVE BACTERIA

BACKGROUND AND PRIOR ART

We disclose herein DNA vectors useful for genetic engineering manipulations of a wide range of gram-negative bacteria, and methods for genetically modifying a wide range of gram-negative bacteria using the vectors disclosed herein.

The field of genetic engineering of microorganisms, including recombinant DNA technology, has developed in large measure on the basis of a vast store of detailed, basic knowledge of the genetics of *Escherichia coli* (hereinafter "*E. coli*") and an extensive array of DNA vectors, plasmids, and phages specifically developed with the aid of such knowledge for use in *E. coli*. Although *E. coli* is itself classified as a gram-negative bacterium, most of the DNA vectors and phages developed for use in *E. coli* are unsuitable for use in other gram-negative bacteria, outside a relatively limited group of bacteria closely related to *E. coli*, for example, Salmonella. Nevertheless, there are many gram-negative strains of current commercial utility, the genetic modification of which will provide substantial economic benefit. Examples of such gram-negative strains include members of the following genera: Rhizobium, Agrobacterium, Pseudomonas, Klebsiella and Azotobacter.

There are several barriers that prevent the direct use of *E. coli* vectors and phages in a broad range of gram-negative bacterial strains. One such barrier is the fact that most of the plasmids commonly used as vectors in *E. coli* are unable to replicate normally in most other gram-negative strains. Another barrier is that efficient plasmid transfer by conjugation between *E. coli* and other gram-negative strains, or between other gram-negative strains, does not occur with most widely used *E. coli* vectors. Furthermore, other means for introducing DNA into most gram-negative strains are poorly developed outside of *E. coli* and its close relatives (hereinafter referred to as the *E. coli* group). Transformation of gram-negative strains outside of the *E. coli* group has been demonstrated in some instances; however, the reported efficiencies of transformation have been much lower in most cases than those obtainable with *E. coli*. While it is possible that higher frequencies of transformation could be obtained for individual gram negative strains by extensive trial and error modification of transformation conditions, it would be desirable to develop vectors that can be transferred by general means applicable to a wide range of gram-negative bacteria.

The drug-resistance plasmid RP4 is known to be transferable across a broad range of gram-negative host bacteria [Datta, N., et al., J. Bact. 108, 1244 (1971); Datta, N., and R. W. Hedges, J. Gen. Microbiol. 70, 453(1972); Olsen, R. H., and P. Shipley, J. Bact. 113, 772 (1973); and Beringer, J. G., J. Gen. Microbiol. 84, 188 (1974)]. Modifications to RP4, to make it useful for genetic manipulation of gram-negative strains, have been reported in the prior art. In particular, RP4 has been modified for use as a vehicle for transposon mutagenesis. Beringer, J. E. et al., Nature 276, 633 (1978) reported the transfer of the transposon Tn5 to Rhizobium using pPH1, a broad host range plasmid of the IncP incompatibility group containing Tn5 and DNA of bacteriophage Mu inserted into the plasmid. Transfer was effected by conjugation between *E. coli* carrying pPH1 (with inserted Mu and Tn5) and a recipient Rhizobium strain. The effect of the Mu insertion was to render the plasmid unstable in the recipient strain so that the transferred plasmid was ultimately eliminated. The transposon could be rescued in recipient cells in which a translocation had occurred prior to elimination of the plasmid. Plasmids constructed in this manner have been termed "suicide plasmids." The use of such plasmids to introduce random nutations into Rhizobium strains has been reported by Meade, H. M., et al., *J. Bact.* 149, 144 (1982), and in *Agrobacterium* by VanVliet, F. B., et al., *Plasmid* 1, 446 (1978).

A number of difficulties have been found to be associated with the use of RP4, or other plasmids of incompatibility group P, carrying the Mu genome and Tn5 in transposon mutagenesis. In some instances, the yield of transconjugants was very low, as measured by the acquisition of a drug resistance associated with the transposon. In many cases, the frequency of a transferred drug resistance was not significantly higher than the spontaneous resistance frequency. In other cases, stably replicating derivatives of the "suicide plasmid" arose, presumably by a deletion of the Mu insert. Such mutant plasmids simulate Tn5 transposition events and it is very time consuming to distinguish between Tn5 insertions and other phenomena, such as the acquisition of a stably replicated plasmid. Furthermore, it was frequently the case that mutations occurred, not only by transposon insertion into the recipient genome, but also by transfer of the Mu phage DNA from the plasmid to the recipient genome. Mutations caused by Mu insertion occurred at sites remote from the transposon insertion site and could not be cloned subsequently, since no readily identifiable marker was associated with a Mu insertion.

In order to facilitate discussion of the invention, the following definitions are provided:

Replicon: a fundamental unit of replication comprising all the genetic elements sufficient to confer autonomous replication in a bacterial cell, together with the DNA whose replication is controlled thereby. The bacterial chromosome, plasmids and phage DNA's are examples of replicons existing in a bacterial cell. Individual replicons differ in the extent to which they are functional in different host cell species. Many of the replicons commonly employed as plasmids for genetic engineering are functional only in bacteria of the *E. coli* group. Others, such as RP4, are able to replicate in a wide range of gram-negative bacterial hosts.

oriT: Site of origin of transfer replication. The mechanism of DNA transfer by bacterial conjugation includes a replication of the plasmid in which a break is introduced into one strand of duplex plasmid DNA, DNA replication then commences at the site of the break, together with transfer of the cut strand to the recipient cell. Some authors have used the designation nic, to indicate the site of the single-stranded break which initiates transfer replication. The term nic is considered to be equivalent to oriT.

Mob-site: A genetic locus necessary for mobilization of a plasmid transferrable by bacterial conjugation. The Mob-site is believed to include oriT. The Mob-site is considered to be the target locus of certain trans-acting functions coded by tra genes. The existence of a Mob-site is a necessary condition for transfer; however, the tra functions must also be provided. Since the latter act in trans, the genes which code for them may be located elsewhere in the cell; for example, on another replicon.

Tra functions and Mob-sites also differ with respect to host range. For example, the tra functions and Mob-site of the F factors are limited in function to conjugal transfers between members of the *E. coli* group. By contrast, the tra functions and Mob-site of the plasmid RP4 permit its conjugal transfer over an exceedingly wide range of gram-negative organisms.

Mob-site segment: As defined herein, the term "Mob-site segment" means that portion of a plasmid which includes the Mob-site but lacks DNA encoding operative tra functions or replication functions.

The genetic analysis and isolation of genes have been greatly facilitated in recent years by the use of transposons. Transposons are special DNA segments which have certain structural features and carry within them certain genes which enable them to be transferred as a unit in a random fashion from one genetic locus to another, with a characteristic frequency. Typically, a transposon will contain one or more drug-resistance genes. These provide convenient selection markers to identify the presence of the transposon and to facilitate cloning of any DNA segment containing a transposon. Insertion of a transposon may occur within a gene, resulting in loss of function for that gene. Transposon mutagenesis, combined with restriction site mapping and cloning provides an extremely powerful and rapid technique for genetic and physical analysis of an organism, together with the ability to clone a desired gene of the organism. Until recently, the techniques of transposon mutagenesis and molecular gene cloning have been restricted to *E. coli* and closely related organisms.

The techniques have been employed, as described, supra, in a variety of other gram-negative bacteria. The prior art attempts to apply these techniques generally have been limited by the difficulties previously described. The present invention discloses the construction and use of new vector plasmids that facilitate in vivo manipulation by transposon mutagenesis and provide techniques for site-specific introduction of a foreign gene or transposon. These techniques are generally applicable across a wide range of gram-negative organisms.

SUMMARY OF THE INVENTION

The invention is based upon modifications to known *E. coli* vector plasmids rendering them mobilizable but not self-transmissible. A mobilizable plasmid is one which is transferrable by bacterial conjugation from a donor cell containing the plasmid to a recipient hose cell, in the presence of tra functions in the donor cell. A plasmid is self-transmissible if the tra functions are coded by DNA of the plasmid itself. A plasmid is nonself transmissible if it lacks DNA coding for operating tra functions and therefore depends, for conjugational transfer, on tra functions supplied exogenously, either on another plasmid or on the host chromosome. The term "*E. coli* vector plasmid" includes generally any of the autonomously replicating plasmids recognized by those of ordinary skill as useful in genetic engineering, cloning, gene mapping and gene transfer and gene expression in connection with *E. coli* or members of the *E. coli* group, comprising a replicon whose functional range is limited to the *E. coli* group. Examples of *E. coli* vector plasmids include, but are not limited to, pMB9, pBR322, pBR325, pKB111, pUC-8, pUC-9, pACYC184, pACYC177, pSC101, and the like.

The usual *E. coli* vector plasmids, such as pBR325 (Bolivar, F. el al., Gene 2, 95 (1977)) or pACYC184 (Chang, A. C. Y. and Cohen, S. N., *J. Bact.* 134, 1141 (1978)) are neither self-transmissible nor efficiently mobilizable. These and other vector plasmids that replicate only in bacterial strains of the *E. coli* group have been modified as disclosed herein to contain the Mob-site of the broad host range plasmid RP4. The modification renders them mobilizable but not self-transmissible. In order to carry out this construction in an efficient manner and to facilitate the transfer of such modified vectors to a wide range of gram-negative recipients, we have also constructed mobilizer strains of *E. coli* which provide the tra functions for the conjugal transfer of these plasmids. The plasmids are unable to replicate after transfer to a gram-negative host (outside the *E. coli* group) and only those genetic elements capable of becoming integrated with the stable DNA component of the host, either chromosomal or plasmid, will remain after several rounds of host cell replication. Integration may occur as by transposon transposition or by recombination between homologous regions. The plasmid used to transfer the gene or transposon to the recipient cell cannot replicate therein and is therefore lost after a few generations of cell growth. The described vectors are widely applicable for transposon mutagenesis, preferably in combination with the mobilizer strains described herein. The vectors are also especially useful for site-directed transposon mutagenesis and also for site-specific gene transfer in a wide variety of gram-negative organisms.

DETAILED DESCRIPTION OF THE INVENTION

Figure 4:
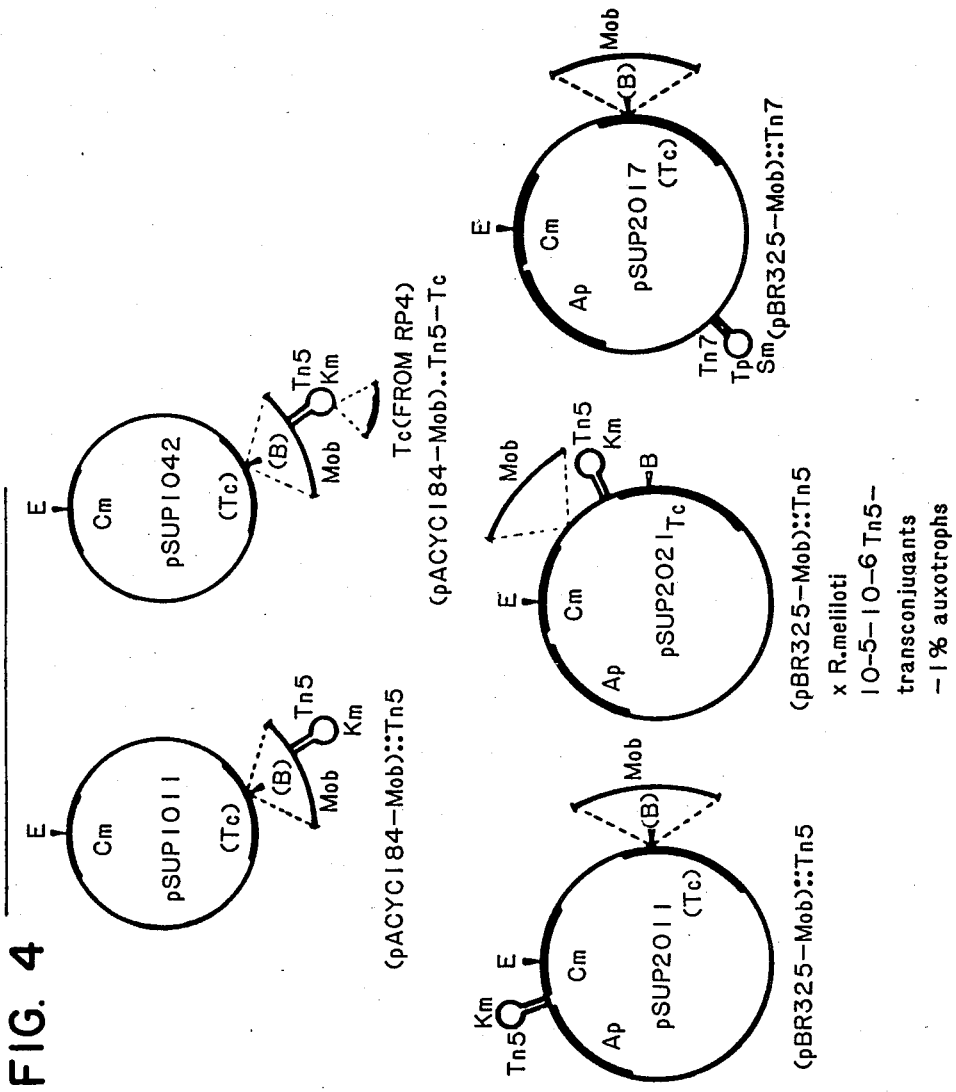

The basic elements of the vector system described herein include an *E. coli* vector, at least that part which provides the replication functions, a DNA fragment comprising the Mob-site of a broad host range plasmid such as RP4 combined therewith, and selection means permitting selection for a plasmid comprising said Mob-site. Suitable *E. coli* vectors are those which are derived from replicons that cannot replicate in bacterial strains outside the *E. coli* group. As a practical matter, such vectors include essentially all the *E. coli* vectors commonly employed for genetic engineering including, for example, pACYC184, pACYC177, and pBR325. It is possible, of course, to employ as a minimum that portion of an *E. coli* vector that provides the replication functions. However, it will be understood that the vectors also provide drug-resistance genes useful for selection and a number of useful and well characterized insertion sites, all of which are highly advantageous in genetic engineering work. Therefore, the preferred construction includes the entire *E. coli* vector, or a major part thereof, combined with a Mob-site.

A segment of DNA comprising a Mob-site may be obtained, in principle, from any plasmid that is mobilizable in a broad range of gram-negative host strains. For convenience, we have employed RP4 as a Mob-site source; however, other broad host range plasmids such R751 may also be used. A fragment comprising a Mob-site should not include replication functions, since these are provided by the *E. coli* vector. It will be readily appreciated that a vector comprising broad host range replication functions could not function as a Class I vector, as defined herein. DNA fragments of such a plasmid may be contained by any technique providing DNA fragments in the range of 100 to 2000 base pairs (bp). The exact size of the Mob fragment of RP4 is unknown except that it is not greater than 2000 bp. It is preferred to use digestion with a restriction enzyme that produces fragments suitable for ligation with restriction endonuclease-cut *E. coli* vector DNA. We prefer for this purpose the restriction endonuclease Sau3A. Sau3A cleavage sites occur frequently in most plasmids, and DNA fragments generated by Sau3A cleavage are readily ligated to linear vector DNA, either produced by Sau3A cleavage or by BamH1 endonuclease. Other expedients known in the art, including blunt-end ligation and the use of linker oligonucleotides to provide suitable end groups for joining may also be employed, as will be appreciated by those of ordinary skill in the art.

The resulting plasmids of the present invention are mobilizable but not self-transmissible. Transfer of a mobilizable, non-self-transmissible plasmid by bacterial conjugation requires the presence of tra functions, provided by a source exogenous to the plasmid.

Selection for a suitable recombinant vector comprising a Mob-site is carried out in a bacterial strain which permits transfer of Mob-site containing vectors. Such a selecting strain must be capable of providing the tra functions that operate on the Mob-site employed. The tra functions can be carried on a plasmid such as an RP4 derivative, but such selections have the disadvantage that the RP4 derivative itself will be transferred in addition to the desired plasmid. The preferred selection means is an *E. coli* cell line constructed to contain an RP4 derivative integrated into the chromosome. If two different derivatives of plasmid RP4 are forced to coexist in a recA-deficient *E. coli* strain (which cannot remove the incompatibility by recombination to cointegrate the two plasmids), the cells grow very poorly under selection conditions that demand the presence of both plasmids. Such selection conditions might be, for example, the presence of two antibiotics in the growth medium, resistance genes for each being provided by each of the incompatible plasmids. In rare cases normally growing colonies can be isolated, some of which contain one of the two incompatible RP4 derivatives integrated in the chromosome. We have taken advantage of such incompatibility reactions to enforce the integration of RP4 plasmids into the chromosomes of *E. coli* strains. The transfer genes of the integrated RP4 derivatives are still expressed, and can be used in conjugation experiments to mobilize vector plasmids carrying the RP4-specific Mob-site. This type of donor strain is termed a mobilizing strain. Using a mobilizing strain, a Mob-site containing plasmid can be selected, following transformation, by growth in the presence of a first antibiotic corresponding to a resistance gene on the plasmid, followed by mating and growth of the recipient strain in a second antibiotic in addition to the first, resistance for the second antibiotic being provided by an endogenous gene of the recipient.

For transposon mutagenesis using the described vectors, it is necessary in addition to include a transposon in the plasmid. We have used for convenience Tn5 which carries a gene for kanamycin resistance. Selection is based upon the acquisition of kanamycin resistance in a mobilizable plasmid having at least one other drug-resistance marker so that its presence in a recipient cell can be selected. When the mobilizable plasmid is introduced, by transformation, into a host cell rendered kanamycin resistant by the presence of Tn5, transformants can be selected by the presence of the drug-resistance introduced by the plasmid. During the growth of such cells, there is a finite probability that the transposon will be transferred to the mobilizable plasmid, and that its site of insertion will be such that no essential plasmid functions are lost, in particular, its replication functions, Mob-site and drug-resistance marker. The plasmid can then be mobilized by introducing an RP4 derivative by conjugation into the Tn5-containing, transformed cells. It will be understood that the introduced RP4 derivative must be so modified that it carries no active drug-resistance genes of the same sort used to select for the presence of Tn5 or the mobilizable plasmid. For example, if the mobilizable plasmid carries streptomycin resistance and the transposon is Tn5, the introduced RP4 derivative must not carry active genes coding for either streptomycin or kanamycin resistance. Following RP4 introduction, the mobilizable plasmid will be rapidly mobilized itself and can be transferred, via a second conjugation step, to a suitable recipient, preferably one which can be independently selected, for example by carrying a third drug-resistance trait not otherwise present in the system. If, for example, the recipient is nalidixic acid-resistant, transconjugants that have received the mobilizable plasmid containing a Tn5 insertion will be nalidixic acid-resistant, kanamycin resistant and resistant to the antibiotic whose resistance gene was initially present on the mobilizable plasmid. It will be understood that other selections schemes can be devised by those of ordinary skill in the art, taking advantage of the availability of transposons, selection markers and recipient strains which may now be or later become available. The resulting plasmid will have, in addition to replication functions with a narrow host range, an inserted Mob-site and inserted transposon. We refer to vectors having narrow host range of replication and a Mob-site providing transferability to a wide host range as Class I vectors. If a Class I vector is further modified by insertion of a transposon, it is designated a Class I-Transposon vector. Class I vectors may be further modified by means generally available to those of ordinary skill in the art, to provide additional desired functions. For example, a cos site may be introduced to provide a Class I cosmid vector.

The Class I vectors are generally useful to transfer any desired segment of DNA into a wide range of gram-negative recipient host strains. Since the vector will not replicate in the recipient host, the continued presence of the transferred gene in the recipient host will depend either on recombination with the host genome or host plasmid, or, in the case of a transposon, on transfer of the transposon to the host genome or plasmid. Therefore, Class I transposon vectors are generally useful for transposon mutagenesis of gram-negative bacterial. The ability to carry out such mutagenesis is the critical first step leading to the cloning of useful genes from gram-negative organisms, as the following illustration demonstrates. Bacterial of the class Pseudomonas are gram-negative organisms displaying a wide variety of metabolic capabilities. Many strains are uniquely capable of producing enzymes that catalyze complex organic reactions such as the degradation of toxic waste substances which may otherwise persist in the environment for long periods of time. The gene coding for an enzyme catalyzing such a degradation reaction can be identified by transposon mutagenesis, using a Class I transposon vector described herein. A mutant strain of Pseudomonas carrying the gene for the desired enzyme mutated by transposon insertion is readily isolated by selecting simultaneously for loss of the gene function and for acquisition of drug resistance carried by the transposon. Subsequent steps, which can all be carried out as matters of routine to those ordinarily skilled in cloning, lead to the isolation of a DNA segment comprising the mutated gene, the use of the isolated segment as a probe to isolate non-mutated alleles of that gene and to carry out structural analyses, including restriction mapping and DNA sequencing, can lead ultimately to the cloning of the desired gene, its transfer to and expression in a desired host strain, and the isolation of the desired enzyme in the desired quantities, all by means of a variety of expedients well understood and well characterized in the art. The Class I vectors therefore provide the means for carrying out the crucial first step of such a chain of events and now open up the possibility for more broadly exploiting the vast potential of the gram-negative organisms that has heretofore been possible.

Site-specific mutagenesis and site-specific gene transfer into recipient gram-negative organisms can be accomplished using the described Class I vectors. These procedures depend on the presence, in the Class I vector, of DNA segments homologous with segments in the recipient cell. When such vectors are transferred into the recipient cell, recombination can occur, between homologous segments on the vector and the host cell DNA. A single recombination event leads to co-integration of the entire vector with the host chromosome. A double recombination event yields replacement of a segment of the chromosomal DNA with the homologous segment from the vector. Such events will be detectable if a selection marker is incorporated within the region of homology. For example, if the region of homology contains a transposon carrying a drug-resistance marker, double homologous recombination yields a site-specific mutation selectable by the drug resistance carried by the inserted transposon. Similarly, the region of homology can be modified by the insertion of a new gene, foreign to the recipient, which is then incorporated into the recipient genome following the double homologous recombination events. The Class I vectors therefore provide a means for genetically engineering a wide range of gram-negative organisms, so that many of the useful properties of these organisms, e.g., ability to grow under unusual environmental conditions, can be exploited.

The construction of specific Class I vectors, their selection and use in specific instances are described in detail in the following examples. The abbreviations used in the examples and elsewhere in the specification are those commonly accepted for publication in standard journals such as those cited herein. When not otherwise specified, reagents and materials described herein are obtainable from commercial sources. Unless otherwise specified, restriction enzymes, DNA ligase and other enzymes were used under conditions specified by the manufacturer or as set forth in the referenced published procedures. Where not otherwise specified, standard procedures, such as those set forth in *Methods in Enzymology* Vol. 68, R. Wu, Ed. (Academic Press, New York 1979) were employed.

EXAMPLE 1

Construction of a Mobilizing Strain

Two derivatives of plasmid RP4 were forced by the choice of selection conditions to coexist in a recA$^-$ *E. coli* host. RP4-2-Tc::Mu was derived from RP4-2 by insertion of phage Mu into the tetracycline resistance gene of RP4-2. (See U. B. Priefer, et al., in *Antibiotic Resistance, Transposition and Other Mechanisms*, (S. Mitshuhashi, L. Rosival and V. Krcmery, eds.) Springer Verlag, Berlin (1980), page 91 and R. Simon, ibid., page 35, for description of RP4-2 and the general methodology of Mu insertion.) Plasmid RP4-2-Tc::Mu is ampicillin-sensitive (Ap$^s$), tetracycline-sensitive (Tc$^s$), kanamycin-resistant (Km$^r$) and Tra$^+$. The plasmid was introduced into a recA$^-$ strain of *E. coli* by conventional conjugation. The recA$^-$ strains used in this study were CSH52, (Miller, J. H., *Experiments in Molecular Genetics*, Cold Spring Harbor Laboratory (1972); C600(recA), (Appleyard, R. K., Genetics 39, 440 (1954); parent strain: ATCC (#23724); and *E. coli* 294(recA), (Cold Spring Harbor Laboratory, New York; parent strain: ATCC #31446). Both C600 and 294 were made recA$^-$ by cotransduction of a known RecA$^-$ deletion mutant with a closely linked selectable marker identified by Tn10 insertion, using phage P1 as the transducing agent. Approximately 50% of Tc$^r$ transductants were RecA$^-$.

The second RP4 derivative employed was pSR120, a fusion product of plasmids pSR100 and ColE1. pSR100 is a "mini RP4", described by Simon et al., supra, isolated as a deletion of RP4 lacking kanamycin resistance and tra functions. pSR120 was derived from pSR100 and ColE1 by joining the two at their unique EcoR1 sites, after digestion with EcoR$_1$ endonuclease and rejoining with DNA ligase. pSR120 was Ap$^r$ and Tc$^r$.

The plasmid pSR120 was introduced into a recA$^-$ strain of *E. coli* containing the plasmid RP4-2-Tc::Mu by transduction with phage P1. The cells were plated on medium containing 25 mg/l kanamycin and 5 mg/l tetracycline. The initial selection yielded several hundred colonies which were very small, indicating poor growth. However, after prolonged incubation, up to three days, a few normal-sized colonies were observed. Cultures derived from these normally-growing colonies were further characterized by gel electrophoretic analysis of plasmid DNA and ability to transfer chromosomal genes. In this manner it was possible to identify strains which retain the Km$^r$ and Tra$^+$ phenotype but which lacked RP4-2-Tc::Mu, indicating that the latter plasmid was integrated in the chromosome.

The plasmid pSR120 was cured from strains containing RP4-2-Tc::Mu integrated in the chromosome. The strain to be cured was grown for about 40 generations in LB medium (Luria broth) (Miller, J., *Experiments in Microbial Genetics*, Cold Spring Harbor Laboratory, New York), containing 100 mg/l acridine orange (AO). After the AO treatment, the culture was enriched for Tc$^s$ cells by incubation in the presence of 5 mg/l tetracycline and 100 mg/l cycloserine. Growth in the presence of tetracycline was lethal to Tc$^r$ cells in the presence of cycloserine. The cycloserine enrichment procedure was repeated twice. Gel electrophoretic analysis of plasmid DNA isoated from Tc$^s$ clones showed that pSR120 was lost. Three clones have been isolated and characterized as described, and their characteristics are shown in the following table:

| strain number | integrated plasmid | resistance markers RP4 | chrom. | other important properties |
|---|---|---|---|---|
| S 68-7 | RP4-2 (Tc::Mu) | Km | Sm | Thi, Pro, His, su$^-$ |
| SM 10 | " | Km | — | Thi, Thr, Leu, su$_{III}$ |
| S 17-1 | RP4-2(Tc::Mu)(Km::Tn$^7$) | Tp-Sm | — | Pro, res$^-$ mod$^+$ |

Strain S68-7 was obtained using *E. coli* CSH52 as the recA⁻ host, strain SM10 was obtained using *E. coli* C600 and S17-1 was obtained from *E. coli* 294(recA⁻). In addition, in strain S17-1, the Km$^r$ was abolished by a Tn7 insertion. Strain S17-1 carries resistance to trimethoprim (Tp) and Streptomycin (Sm, provided by Tn7). A schematic representation of the construction of a mobilizing strain as described herein, is shown in FIG. 1.

EXAMPLE 2

Construction of Mobilizable Vector Plasmids

The following constructions were based on the strategy of inserting random fragments of RP4, generated by partial Sau3A digestion, into the BamHI site of an *E. coli* vector, e.g., pACYC184 and pBR325. The hybrid plasmids containing the RP4-specific Mob-site were identified by mating experiments using a mobilizing strain, constructed as described in Example 1, as donor.

Partial digestions of RP4 DNA with Sau3A were carried out under reaction conditions empirically chosen to provide an optimum size range of RP4 fragments. The conditions of buffer, reaction time and temperature were as described by the manufacturer of the restriction enzyme. However, the amount of enzyme employed was reduced by making a series of dilutions of the restriction enzyme. The resulting mixtures of fragments were subjected to agarose gel electrophoresis to determine the distribution of fragment sizes. Digests yielding RP4 DNA fragments mostly smaller than about 3kb were used for the subsequent ligation reaction. Some variation was observed between batches of enzyme. In one experiment, a 1:125 dilution of Sau3A endonuclease yielded a fragment distribution in which the majority of fragments appeared to be greater than 2 kb and a substantial portion were greater than 3 kb, while a 1:100 dilution of the enzyme yielded fragments the majority of which were smaller than 3 kb.

The vector plasmid, either pACYC184 or pBR325 were linearized by digestion with BamHI endonuclease, using standard reaction conditions for complete digestion. Since these vector plasmids possess a unique BamHI site, the resulting digestion yielded linear molecules of uniform size.

In the ligation reaction, 20 µl of partial Sau3A-digested RP4 DNA prepared as described, supra (about 20 µg/ml) and 10 µl BamHI digested pACYC184 (or pBR325) DNA, about 20 µg/ml, were mixed with 3 µl ATP (1 mg/ml) and 1 µl DNA ligase in a standard DNA ligase reaction buffer (*Methods in Enzymology*, Vol. 68, supra.) incubated at room temperature for 3 hours. The resulting hybrid plasmids were used to transform the mobilizing strain S68-7 (Example 1) by a standard transformation procedure (Miller, J. supra). Transformants were selected by growth on agar plates containing PA-medium [17.5 g/l Penassay broth (Difco Laboratories, Detroit, Mich.)] supplemented with 100 mg/l chloramphenicol. Several hundred colonies were picked and grown in mixed liquid culture to mid-log phase, constituting a donor culture for subsequent mating.

The recipient strain was a Nalidixic acid-resistant (Nx$^r$) strain of *E. coli* C600. Approximately 5×10⁸ donor cells were mixed with 10⁹ recipient cells, collected on a nitrocellulose filter and incubated on pre-warmed PA medium for 2 hours at 37° C. The cells were then re-suspended in liquid medium and aliquots were spread on agar selection plates containing PA medium supplemented with chloramphenicol (100 ml/l) and nalidixic acid (100 mg/l). The plasmid construction and selection system is shown schematically in FIG. 2. Selection for combined chloramphenicol and nalidixic acid resistance yields cells in which the recombinant plasmid containing the Cm$^r$ gene has been transferred to the Nx$^r$ recipient. In principle, only mobilizable recombinant plasmids could be transferred.

From the resulting colonies, a selected clone was characterized and found to contain a mobilizable derivative of pACYC184. The plasmid was mobilized by the RP4 transfer functions with a frequency of 100% in *E. coli* matings. As shown by restriction analysis, the plasmid contained a DNA insert of 2.6 kb. The resulting plasmid was designated pSUP101.

Using the same procedure, the Mob-site of RP4 was cloned into the vector plasmid pBR325. The resulting mobilizable derivative, designated pSUP201, was found to contain an insert of only 1.9 kb, yet was as efficiently mobilized as pSUP101. Therefore, the Mob-site was contained within a DNA fragment not larger than 1.9 kb.

Partial restriction and genetic maps of pSUP101 and pSUP201 are shown in FIG. 2.

EXAMPLE 3

Vector Construction With Inserted Mob-site and Preserved BamHI Site

In these constructions, the vector plasmid pBR325 was converted to full-length linear DNA by partial Sau3A endonuclease digestion. Since the vector possesses numerous Sau3A sites, and digestions are presumably randomly distributed over such sites, use of digestion conditions which yield a maximum proportion of full-length linear molecules provides the possibility for insertion of a Mob-site fragment at any Sau3A site on the vector plasmid. DNA fragments containing the Mob-site were obtained by partial Sau3A digestion as described in Example 2 with the exception that pSUP101 was used as the source of the Mob-site fragment. Selection for mobilizable pBR325 hybrid plasmids were as carried out using the mobilizing strain S68-7 (Example 1) as described in Example 2.

In order to determine optimal reaction conditions for partial Sau3A digestion of pBR325, constant amounts of plasmid DNA were treated with serial dilutions of Sau3A endonuclease. The digests were then analyzed by agarose gel electrophoresis. The optimum conditions for digestion were defined as those giving the maximum proportion of linear DNA molecules of full length, compared to smaller fragments and circular, uncut molecules. The optimal conditions were then scaled up to carry out digestion of about 20 µg of pBR325 DNA. The digests were then enriched for linear molecules by centrifugation in cesium chloride containing ethidium bromide. In a typical centrifugation, 8 ml of DNA solution was mixed with 8 g CsCl chloride and 0.35 ml ethidium bromide solution (20 mg/ml in 10 mM Tris, 1 mM EDTA, pH 7.5), centrifuged for approximately 48 hours at 34,000 rpm in a Beckman Instruments (Fullerton, Calif.) Ti 50 rotor at 20° C. After centrifugation, fractions from the gradient containing linear pBR325 plasmids were recovered, extracted with isopropanol to remove ethidium bromide and dialyzed against 10 mM Tris buffer pH 7.5 containing 1 mM EDTA.

A DNA fragment containing the Mob-site was obtained by partial digestion of pSUP101 DNA, described supra in Example 2, using partial Sau3A digestion conditions as described therein.

The purified linear pBR325 DNA was mixed with the Sau3A fragments of pSUP101 and incubated with DNA ligase to join the fragments, using standard ligation conditions as described supra, Example 2. The ligation mixture was used to transform the mobilizing strain S68-7 (Example 1). Transformants were selected for ability to grow on plating medium containing tetracycline, 10 µg/ml. Several hundred Tc$^r$ colonies were mixed and grown in liquid culture into the log phase. Screening for mobilizable hybrid plasmids was carried out as described, supra Example 2, by mating the mixed culture of transformants with a Nx$^r$ C600 derivative of E. coli. Two different mobilizable pBR325 derivatives were isolated, designated pSUP202 and pSUP203. These isolates were distinguished by the fact that the Mob-sites were inserted at different loci. The restriction and genetic map information for these plasmids is shown in FIG. 3.

EXAMPLE 4

Insertion of Tn5 Into Mobilizable Plasmids

A double-donor mating was used to transfer the transposon Tn5 into plasmid pSUP101 (Example 2). Donor No. 1 was simply an E. coli strain (C600) containing RP4-Km::Mu, an RP4 derivative in which kanamycin resistance is destroyed by Mu phage insertion. Donor strain No. 2 was a derivative of E. coli C600 containing Mu and Tn5 inserted in the chromosome and into which pSUP101 had been introduced by transformation. Donor No. 1 was used merely as a source of RP4 transfer functions which, following introduction into Donor No. 2, acted to mobilize pSUP101. The recipient strain, also E. coli C600, was a Nx$^r$ strain. The principle of operation of the double-donor mating system was based on the expectation that Tn5 would transfer with a certain spontaneous frequency from its chromosomal location in Donor No. 2 to pSUP101. The latter, carrying Tn5 with its associated Km$^r$ gene, would confer transferrable kanamycin and chloramphenicol resistance to a recipient strain upon mobilization and transfer from Donor No. 2 to the recipient. The recipient was provided with an independent drug-resistance gene Nx$^r$ to enable it to be selectively grown in the presence of Donors 1 and 2.

In the first mating, $5 \times 10^8$ logarithmically growing cells of Donor 1 and Donor 2 were mixed and incubated on a nitrocellulose filter on a prewarmed PA plate for 30 minutes at 37° C. This mating provided cells of Donor 2 with the RP4 transfer functions needed for mobilization of pSUP101, but was carried out for a minimum time to reduce the likelihood of Tn5 insertion in RP4.

The second mating was commenced with the introduction of $2 \times 10^9$ recipient cells (E. coli C600 Nx$^r$ and Mu-immune) were mixed with the mating mixture of the first mating. This mating mixture was further incubated for 2 hours at 37° C.

The mating mixture was then suspended in liquid medium, aliquots of which were spread onto PA medium containing Cm (100 mg/l), Km (25 mg/l) and Nx (100 mg/l). Colonies able to grow under these selection conditions contained derivatives of pSUP101 carrying Tn5 inserted at various positions. Selected colonies were grown in liquid culture and the plasmid DNA extracted therefrom further characterized by restriction analysis. One such plasmid, designated pSUP1011, was found to possess the Tn5 insertion within the Mob fragment, apparently without interference with the mobilizability of the plasmid. Using the same procedure, Tn5 containing derivatives of pSUP201 and pSUP202 were also obtained. The resulting plasmids are diagrammed in FIG. 4.

EXAMPLE 5

Transposon Mutagenesis Using a Class I Vector

The ability to generate and select for mutants of a gram-negative bacteria is greatly facilitated with use of a Class I vector carrying a transposon. An example of the generation and selection of such mutants was demonstrated using plasmid pSUP2021, a mobilizable pBR325 derivative carrying transposon Tn5, shown in FIG. 4. The plasmid was used to generate auxotrophic mutants of Rhizobium meliloti 2011, a streptomycin resistant (Sm$^r$) strain. Auxotrophic mutants were defined by their inability to grow on a minimal medium which would support growth of the parent strain, and by their ability to grow on a rich medium, e.g., LB broth. Plasmid pSUP2021 was mobilized from E. coli S 17-1 (Example 1) into R. meliloti 2011. The mating was carried out using filter membranes on a rich medium for about 5 hours at 32° C. The cells were then suspended in sterile water and plated onto a selection medium containing 500 mg/l Sm and 100 mg/l Km. The Km$^r$ transconjugants were obtained at a frequency of from $10^{-6}$ to $10^{-5}$ per recipient. Since the Class I vector was unable to replicate in the recipient, the ability of recipient colonies to grow under the selection conditions indicated transfer of the transposon from the Class I plasmid to the recipient genome. About 1-2% of these Tn5-containing clones were auxotrophic mutants. The above described mating also demonstrates the usefulness of the Class I vector for introducing a drug resistance gene carried on a transposon into a recipient gram-negative bacterial strain. An important advantage of the use of transposons for mutagenesis is that it dramatically reduces the number of colonies to be tested to find a particular phenotype which cannot be directly selected.

Once a transposon-induced mutant is isolated, it is a straightforward matter to clone the mutated gene, for example in E. coli, by a "shotgun" cloning procedure coupled with selection for the transposon-encoded drug resistance. The corresponding wild type gene is then isolated from a gene bank, using the cloned mutated gene as a hybridization probe. In addition, DNA sequences adjacent to the wild type gene can also be isolated provided they coexist on a fragment capable of hybridizing with the segment cloned initially.

EXAMPLE 6

Introduction of Foreign Genes Into a Gram-Negative Bacterial Strain

A Class I vector is employed, in connection with the procedures described in Example 4, to isolate a DNA segment containing the promoter and structural gene for a cellulase of P. fluorescens, subsp. cellulosa, a known cellulose degrading organism. In the second step, a Class I vector is used to assist in the isolation of a nonessential region of the chromosome of a nitrogen-fixing species of Azotobacter, preferably by transposon insertion followed by selection for normal growth.

The cloned Azotobacter DNA segment is mapped for restriction site analysis by conventional means in *E. coli*. The cloned cellulase gene is inserted at a site chosen such that it is flanked by Azotobacter DNA sequences on either side. It is preferred to have a drug-resistance gene inserted in proximity to the cellulase gene to provide a means for selecting for the presence of the recombinant segment (containing the cellulase gene and the flanking Azotobacter DNA sequences). The entire composite is cloned into a Class I vector which is subsequently mobilized and transferred to the original Azotobacter strain, followed by selection for the presence of the antibiotic resistance gene in the Azotobacter strain. With a certain probability, the magnitude of which will vary directly with the size of the cloned Azotobacter flanking sequences contained in the Class I vector, recombination within the flanking segments will result in integration of the entire segment including the cellulase gene, into the Azotobacter genome. The resulting organism combined pheno-typically the ability to fix nitrogen and to degrade cellulose.

EXAMPLE 7

Site-Specific Insertion of Foreign DNA Into *R. meliloti*

An EcoRi fragment from *R. meliloti* containing the nifH gene and part of nifD isolated by Ruvkun, G. B. and Auseubel, F. N., *Proc. Natl. Acad. Sci. USA* 77, 191 (1980) was cloned into the mobilizable Class I vector pSUP202 (FIG. 3). The DNA fragment carrying the nifH gene of *R. meliloti* was cloned into the unique EcoRI site. A DNA fragment of 4.2 kb derived from PR4 by partial Sau3A digestion (Example 2) containing the tetracycline resistance gene ($Tc^r$) was inserted into the BglII site of the *R. meliloti* nifDNA fragment. The resulting plasmid was mobilized from *E. coli* S17-1 (Example 1) into a recipient *R. meliloti* strain. Transconjugants selected for $Tc^r$ appeared with a frequency of about $10^{-4}$ per recipient. Further screening for loss of the vector plasmid by sensitivity to ampicillin was carried out. The resulting strain contained a $Tc^r$ gene inserted at a predetermined site adjacent to the nifH gene of *R. meliloti*. As in the previous example, the DNA segment in question was transferred to the recipient genome by double recombination. The introduction of a foreign gene such as a drug resistance gene into Rhizobium at a predetermined locus known to be stable is preferred over the use of a plasmid. Rhizobium strains in general tend to lose plasmids in the absence of selection pressure, particularly during passage through the root nodule, where up to 90% of extraneous plasmids may be lost. The described procedure provides for the site-specific introduction of genes in a manner which insures their stability. Screening for loss of the vector plasmid was carried out to insure that gene transfer occured through a double recombination event, since a single recombination event would lead to cointegration of the entire vector plasmid. Approximately 2% of the $Tc^r$ transconjugants were also $Ap^s$ indicating double recombination and loss of the Class I vector plasmid.

The following strains *E. coli* were placed on deposit with the U.S. Department of Agriculture, Northern Regional Research Center, 1815 North University Street, Peoria, Ill. 61604:

| Strain | NRRL Accession # | Deposit Date |
|---|---|---|
| *E. coli* CSH52/pSUP101 | B-15484 | July 1, 1983 |
| *E. coli* CSH52/pSUP201 | B-15487 | July 1, 1983 |
| *E. coli* CSH52/pSUP202 | B-15488 | July 1, 1983 |
| *E. coli* CSH52/pSUP203 | B-15489 | July 1, 1983 |
| *E. coli* CSH52/pSUP301 | B-15492 | July 1, 1983 |
| *E. coli* CSH52/pSUP401 | B-15494 | July 1, 1983 |
| *E. coli* SM10 | B-15481 | July 1, 1983 |
| *E. coli* S68-7 | B-15482 | July 1, 1983 |
| *E. coli* S17-1 | B-15483 | July 1, 1983. |

We claim:

1. A suicide plasmid that is mobilizable, but not self-transmissible, comprising:
   (a) a first DNA segment containing a replicon functional in *E. coli*; and
   (b) a second DNA segment containing a Mob-site and oriT of a plasmid transferrable by conjugation in the presence of a tra function encoded by a gene that acts in trans and capable of transferring the plasmid to an organism in which said replicon does not function;

said suicide plasmid not containing a gene providing said tra function.

2. A DNA suicide plasmid according to claim 1 further comprising a transposon.

3. A DNA suicide plasmid according to claim 1 further comprising transposon Tn5.

4. A DNA suicide plasmid according to claim 1 comprising the Mob-site of plasmid RP4.

5. A suicide plasmid according to claim 1 wherein said replicon functional in *E. coli* is that of pACYC184.

6. A suicide plasmid according to claim 1 wherein said replicon functional in *E. coli* is that of pACYC177.

7. A suicide plasmid according to claim 1 wherein said replicon functional in the *E. coli* group is that of pBR325.

8. A suicide plasmid according to claim 1 selected from the group consisting of pSUP101, pSUP301, pSUP401, pSUP201, pSUP202, and pSUP203.

9. A suicide plasmid according to claim 1 further comprising a cos site.

10. A suicide plasmid according to claim 1 wherein said plasmid is pSUP205.

11. A bacterial cell containing and replicating the suicide plasmid of claim 1.

12. A bacterial cell according to claim 11 wherein said DNA suicide plasmid further comprises a transposon.

13. A bacterial cell according to claim 11 wherein said DNA suicide plasmid further comprises transposon Tn5.

14. A bacterial cell according to claim 11 wherein said DNA suicide plasmid comprises the Mob-site of plasmid RP4.

15. A bacterial cell according to claim 11 wherein said replicon functional in *E. coli* of said suicide plasmid is that of pACYC184.

16. A bacterial cell according to claim 11 wherein said replicon functional in *E. coli* of said suicide plasmid is that of pACYC177.

17. A bacterial cell according to claim 11 wherein said replicon functional in *E. coli* of said suicide plasmid is tht of pBR325.

18. A bacterial cell according to claim 11 wherein said DNA suicide plasmid is selected from the group consisting of pSUP101, pSUP301, pSUP401, pSUP201, pSUP202, and pSUP203.

19. A bacterial cell according to claim 11 wherein said suicide plasmid further comprises a cos site.

20. A bacterial cell according to claim 19 wherein said DNA suicide plasmid is pSUP205.

21. A method of site-specific mutagenesis in a gram-negative bacterial cell comprising the steps of:
(a) transferring into said bacterial cell a composite DNA plasmid comprising the suicide plasmid of claim 1 further comprising a third DNA segment homologous with a corresponding fourth DNA segment of said bacterial cell, said third DNA segment containing a mutation and a selectable genetic marker; and
(b) incubating said bacterial cell after said transfer under conditions that select for the continued presence of said selectable genetic marker, whereby recombination occurs between said third DNA segment and said fourth DNA segment, said recombination transferring said mutation to a specific site in said bacterial cell.

22. A gram-negative bacterial cell having a mutation made by the method of claim 21.

* * * * *